United States Patent [19]

Cooper

[11] Patent Number: 4,474,734
[45] Date of Patent: Oct. 2, 1984

[54] SYRINGE SHIELD AND CLOSURE STERILIZATION METHOD

[75] Inventor: Murray S. Cooper, Dumount, N.J.

[73] Assignee: Microbiological Applications, Inc., Islamorada, Fla.

[21] Appl. No.: 510,663

[22] Filed: Jul. 5, 1983

[51] Int. Cl.³ .............................................. A61L 2/20
[52] U.S. Cl. ...................................... 422/34; 422/26; 422/28; 604/263
[58] Field of Search ............... 422/295, 297, 100, 102, 422/26, 28, 34; 604/263, 192, 198, 411, 414

[56] References Cited

U.S. PATENT DOCUMENTS

| | | | |
|---|---|---|---|
| 2,551,339 | 3/1949 | Ryan et al. | 604/227 |
| 2,551,414 | 5/1951 | Burnside | 604/227 |
| 2,667,163 | 1/1954 | Smith | 604/195 |
| 2,671,449 | 3/1954 | Dann | 604/227 |
| 2,854,975 | 8/1952 | Cohen | 604/227 |
| 3,549,312 | 5/1968 | Ernst | 422/34 |
| 3,865,236 | 2/1975 | Rycroft | 604/199 |
| 3,878,846 | 4/1975 | Rimbaud | 604/227 |
| 4,068,659 | 1/1978 | Moorehead | 604/159 |
| 4,240,425 | 12/1980 | Akhavi | 604/199 |
| 4,247,517 | 1/1981 | Sanderson et al. | 422/112 |
| 4,365,626 | 12/1982 | House | 604/193 |
| 4,416,417 | 11/1983 | Sanderson et al. | 236/92 R |

FOREIGN PATENT DOCUMENTS

| | | | |
|---|---|---|---|
| 737287 | 8/1968 | Belgium | 422/26 |
| 656699 | 1/1963 | Canada | 422/34 |

*Primary Examiner*—Ernest G. Therkorn
*Assistant Examiner*—Titus B. Ledbetter, Jr.
*Attorney, Agent, or Firm*—Leon E. Tenenbaum

[57] ABSTRACT

A pre-filled syringe-needle assembly in which the needle is covered with a shield-closure unit to assure sterility. Said shield-closure unit comprises a tube which covers the needle and a plug for said tube, one end of said tube being adapted for fitting tightly over the reduced part of the barrel of a syringe, and the other end being covered by the plug, both said end and plug covering it being adapted to provide an air-tight fit between them, said plug being sufficiently long to engage the tip of the needle inside the tube.

1 Claim, 5 Drawing Figures

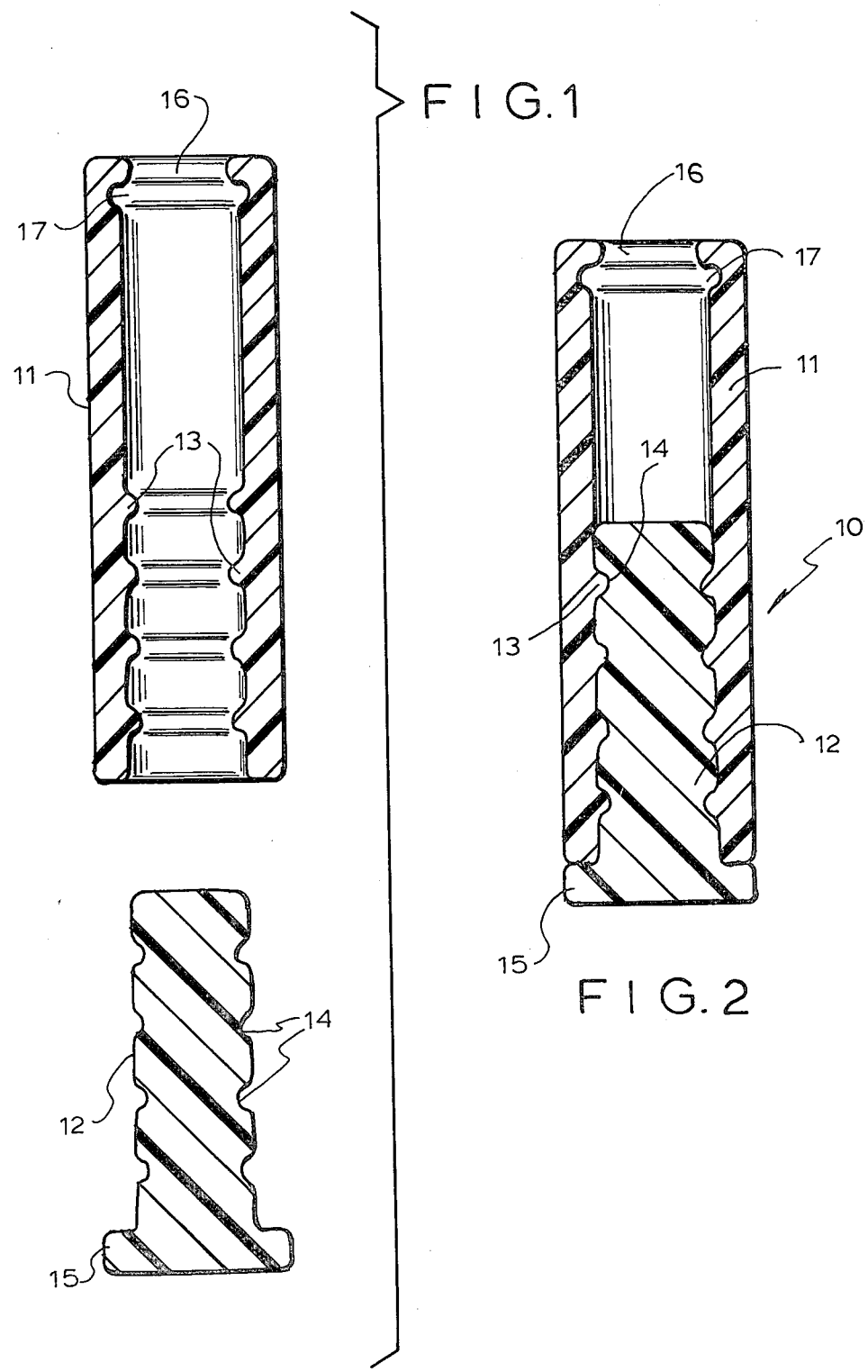

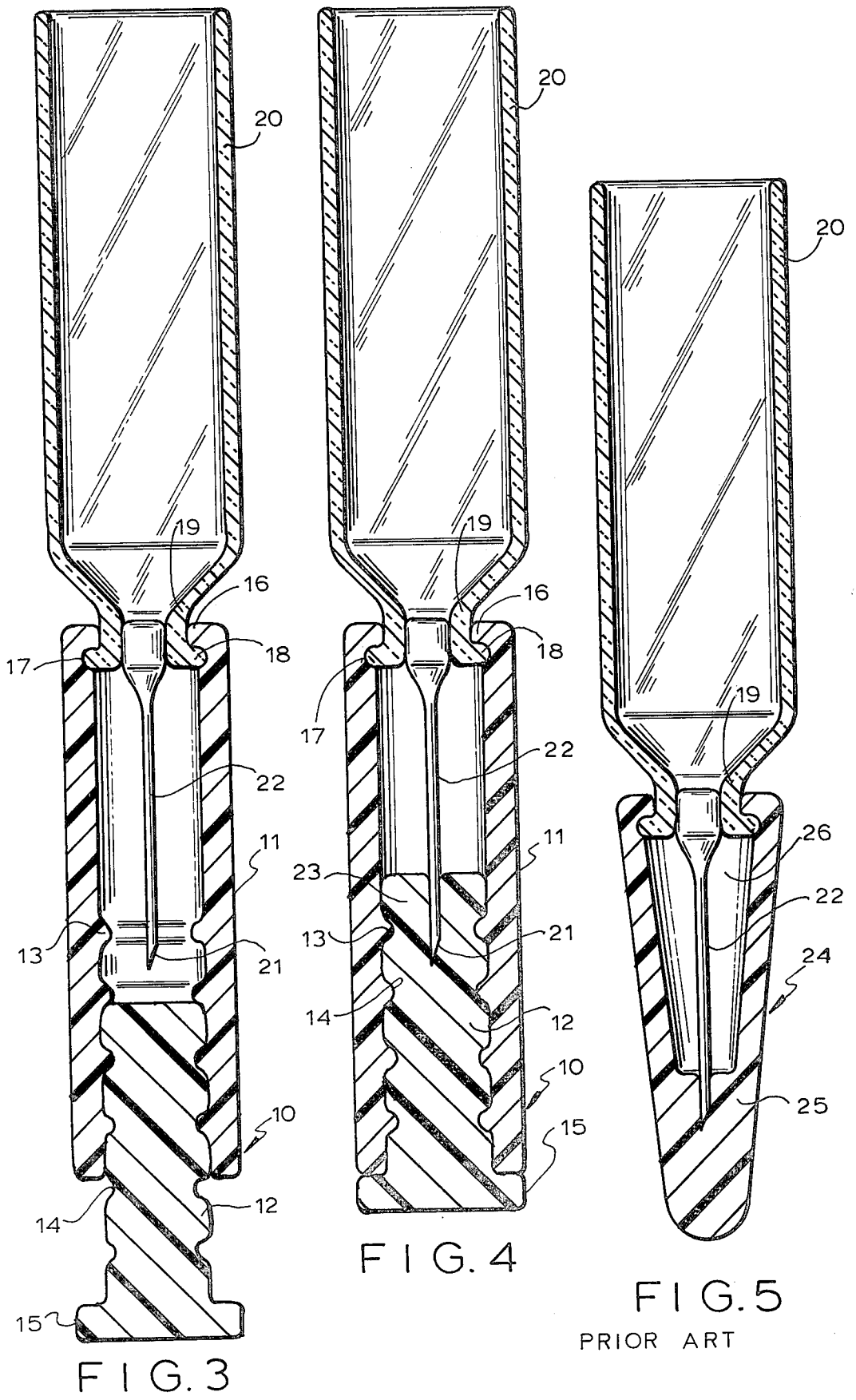

SYRINGE SHIELD AND CLOSURE STERILIZATION METHOD

This invention relates to shields and closures for pre-filled injection syringes. It particularly relates to a combined shield and closure for the needle attached to a pre-filled injection syringe, which enables the injection syringe-needle assembly to be efficiently sterilized prior to filling. It also relates to a method for sterilizing syring-needle assembly units.

BACKGROUND OF INVENTION

A significant portion of injectable sterile liquid medications presently distributed by pharmaceutical manufacturers is in the form of pre-filled injection syringes containing a sterile medicament which had been placed in a pre-sterizilized syringe-needle assembly unit.

The syringe barrel, which serves as the container for the medicament, is usually fabricated from glass in order to comply with compendial and regulatory requirements for purity and stability of the medicament preparation contained therein. Since the active medicament preparation can rarely withstand the sterilization techniques usually employed to sterilize the syringe-needle assembly because of possible degradation and/or inactivation of the active medicament, the syringe-needle assembly unit is separately sterilized prior to the introduction under aseptic conditions of a sterile medicament preparation into the barrel of the sterile syringe, and a plunger (closure) is inserted into the filled syringe barrel by the displacing the air by means of an air outlet tube.

In order to prevent the medicament preparation in the syringe barrel from leaking out through the attached needle, the needle, prior to the sterilization of the syringe-needle assembly unit is imbedded or inserted into a sleeve-closure unit, preferably made of rubber or rubber-like material. This sleeve-closure unit serves to prevent leakage and to cover the entire needle thereby maintaining the sterility of the entire needle. An example of such sleeve-closure unit is shown in U.S. Pat. No. 3,865,236.

In this system the sleeve-closure unit, which covers the entire needle up to the hub, also creates a dead space wherein the sterilizing means cannot readily penetrate. This is particularly true in respect of the tip portion of the needle which is imbedded or inserted into the sleeve-closure unit; since the portion of the needle which directly enters the tissue of the recipient may not be effectively sterilized.

This problem applies to both steam and ethylene oxide sterilization since the sterilizing agent cannot come into direct contact with the portion of the needle covered or otherwise shielded by the sleeve-closure unit. While this problem can possibly be obviated by employing ionizing radiation as the sterilizing means for the syringe-needle assembly unit wherein the needle is covered by the sleeve-closure unit, such sterilizing means are not generally applicable to commonly used disposable glass injection syringes since these means cause the glass to darken.

The concern about the possible lack of sterility in pre-filled syringe-needle units can be seen from the special attention this problem has received in the United States Pharmacopeia (USP) XX and XXI. In the Sterility Test chapter of the USP appears the following statement:

"Pre-Filled Disposable Syringes—Special attention should be directed towards demonstrating that the outside of the needle (that portion that enters the patient) is sterile."

A number of patents cover certain methods or structural features for sterilizing syringe-needle assembly units but these methods and/or structural features do not relate to the syringe-needle assembly units wherein the needle is imbedded in sleeve-closure units. These patents include U.S. Pat. Nos. Re. 25,113; 2,375,929; 2,646,043; 3,122,747; 3,370,588; 3,381,813; 4,148,316 and 4,240,425. These patents provide means for contacting the needle with sterilizing gases; e.g. steam or ethylene oxide, but these means are not suitable for pre-filled syringe-needle assembly units.

THE PRESENT INVENTION

It is, accordingly, an object of this invention to provide a sleeve-closure unit for the needle portion of the pre-filled syringe-needle assembly, which will permit a sterilizing medium to reach all surfaces, both inner and outer, of the needle.

It is another object of this invention to provide a sleeve-closure unit which is adapted to cover and shield the needle after sterilization to maintain its sterility.

It is further object of this invention to provide a method for sterilizing pre-filled syringe-needle assembly units.

Other objects will appear in the description which follows.

In accordance with this invention there is provided a sleeve-closure unit comprised of a tube which fits over and thereby covers and shields the needle, one end of said tube being adapted fit tightly over the reduced end of the syringe barrel in which the needle is being held, and a plug which is inserted into the other of the tube, both plug and tube being adapted to provide an air-tight fit to assure the maintenance of the sterility of the needle.

The tube and plug are preferably fabricated from somewhat resilient materials such as rubber, nylon, polyethylene, polypropylene, polycarbonate and the like, and may be made from the same or different materials. Nylon, high cross-linked polyethylenes and polycarbonates are preferred since they are resistant to steam and ethylene oxide.

The invention will be clearer from the drawings and description which follow. These drawings and the embodiments described in connection therewith are only given by way of illustration and are not to be considered as limiting.

DRAWINGS AND DESCRIPTION OF EMBODIMENTS

Referring to the drawings

FIG. 1 is a sectional side-elevational view of the two-part sleeve closure unit of this invention with the parts separated.

FIG. 2 is a sectional side-elevational view of the two-part sleeve closure unit of this invention with the parts joined.

FIG. 3 is a sectional side-elevational view of the two-part sleeve-closure unit of this invention mounted on the reduced part of the syringe barrel in the position where the tip of the needle exposed.

FIG. 4 is a sectional side-elevational view of the two-part sleeve-closure unit of this invention mounted on the reduced part of the syringe barrel, in position where the tip of the needle is imbedded in the plug.

FIG. 5 (prior art) is a sectional side-elevational view of a syringe-needle assembly with a sleeve-closure unit mounted thereon, of the type of pre-filled syringe now being marketed.

The sleeve-closure unit (10) of this invention is comprised of a tube (11) and a plug (12). One end of the tube is provided internally with a plurality of substantially parallel spaced annular ribs (13) which engage a series of substantially parallel similarly spaced grooves (14) on the plug. The diameter of the plug and the inner diameter of the tube are substantially the same. The plug is preferably provided with a flange (15) which fits against the end of the tube when the plug is fully inserted therein. The substantially same sizes of the diameters, the engagement of the ribs with the grooves, and the flange assure an air-tight fit when the plug is fully inserted into the tube. The opposite end (16) of the tube is provided with means such as an inner groove (17) which engages a flange (18) at the reduced end (19) of the barrel (20). This is one means of securing the tube to the syringe barrel. Other means may include the provision of outer threads on the reduced end of the barrel and inner threads in the tube whereby the tube may be screwed onto the syringe barrel.

In practicing the present invention the plug, as shown in FIG. 4 is partially inserted into the tube which is then fitted onto the reduced part of the syringe barrel, or the steps may be reversed; i.e. the tube fitted first and then the plug partially inserted. The plug must be inserted only to a distance at which it does not contact the end (21) of the needle (22). The entire unit is placed in a sterilization chamber and evacuated. A sterilizing gas such as, for example, steam or ethylene oxide, is then passed in under pressure. The evacuation and introduction of the sterilizing agent may be repeated. The needle, particularly the part of which will enter the patient on injection, is thus fully exposed to the sterilizing medium. The system is evacuated once again. After the sterilizing is completed, the syringe-needle assembly with the shield-closure attached thereto is removed from the sterilization chamber. The partially seated plug will now protect the needle from contamination. The plug which should be sufficiently long to engage the tip of the needle when fully inserted into the tube, is now fully inserted into the tube to have the needle imbedded therein (23). The syringe-needle assembly is thus completely closed at the bottom to prevent leakage and contamination. It is then filled under sterile conditions with a sterile injectable.

In FIG. 5, (prior art), which illustrates the type of unit now being marketed, the shield-cover (24) is secured to the reduced end of the barrel and the needle imbedded (25) in the sleeve-cover prior to sterilization. It can be readily seen that in this system, using a one-piece shield cover, the tip of the needle, particularly its outer portion, cannot be directly reached by the sterilizing agent and hence cannot be truly sterilized. Furthermore, since the system is closed, the sterilizing agent cannot reach the outer surface of the rest of the needle since the agent cannot readily enter the space (26) surrounding the needle.

I claim:

1. A method for sterilizing a pre-filled syringe-needle assembly unit which comprises fitting onto the reduced end of the barrel of the syringe and around the needle a shield-closure unit which comprises a tube which covers the needle and a plug for said tube, one end of said tube being adapted for fitting tightly over the reduced part of the barred of a syringe and the other end being covered by the plug, both said end and plug covering it being adapted to provide an air-tight fit between them, said plug being sufficiently long to engage the tip of the needle inside the tube wherein the plug of the shield-closure unit is partially inserted into the tube to a distance where it does not come into contact with the tip of the needle, evacuating through the open end of the barrel of the syringe the pre-filled syringe-needle assembly unit which has been fitted with the shield-closure unit passing under pressure through said open end of the barrel into the unit a sterilizing gas, evacuating the unit, and after sterilization is completed, fully inserting the plug into the tube so that the tip of the needle enters into and becomes imbedded in the plug.

* * * * *